United States Patent
Gabaldon Hernandez et al.

(10) Patent No.: US 9,448,233 B2
(45) Date of Patent: Sep. 20, 2016

(54) METHOD AND SYSTEM FOR DETECTION OF NATURAL HIGH INTENSITY SWEETENERS THAT CONTAIN HYDROXYL GROUPS

(75) Inventors: Jose Antonio Gabaldon Hernandez, Murcia (ES); Estrella Nunez Delicado, Murcia (ES); Rosa Puchades Pla, Valencia (ES); Angel Maquiera Catala, Valencia (ES); Eva Maria Brun Sanchez, Valencia (ES); Avetik Markosyan, Kuala Lumpur (MY)

(73) Assignee: PureCircle Sdn Bhd, Negeri Sembilan (MY)

( * ) Notice: Subject to any disclaimer, the term of this patent is extended or adjusted under 35 U.S.C. 154(b) by 0 days.

(21) Appl. No.: 14/346,967

(22) PCT Filed: Jun. 22, 2012

(86) PCT No.: PCT/MY2012/000138
§ 371 (c)(1),
(2), (4) Date: Mar. 25, 2014

(87) PCT Pub. No.: WO2013/048227
PCT Pub. Date: Apr. 4, 2013

(65) Prior Publication Data
US 2014/0234876 A1 Aug. 21, 2014

(30) Foreign Application Priority Data
Sep. 27, 2011 (MY) ............... PCT/MY2011/000209

(51) Int. Cl.
*G01N 33/53* (2006.01)
*C07H 15/24* (2006.01)
*C12Q 1/28* (2006.01)

(52) U.S. Cl.
CPC .......... *G01N 33/5308* (2013.01); *C07H 15/24* (2013.01); *C12Q 1/28* (2013.01); *G01N 2400/00* (2013.01)

(58) Field of Classification Search
CPC .. G01N 33/53; G01N 33/66; G01N 2400/00; C07K 16/44; A61K 2039/55583; C07H 15/24
See application file for complete search history.

(56) References Cited

U.S. PATENT DOCUMENTS

| 4,990,443 A | 2/1991 | Huber et al. |
| 5,032,518 A | 7/1991 | Huber et al. |

OTHER PUBLICATIONS

Goodrow et al. Strategies for immunoassay hapten design. In Immunoanalysis of Agrochemicals, ACS Symposium Series, American Chemical Society, Washington, DC, 1995, pp. 119-139.*
Kinghorn et al. A phytochemical screening procedure for sweet ent-kaurene glycosides in the genus *Stevia*. J. Natural Products 1984, vol. 47, No. 3, pp. 439-444.*
Nolli et al. Antibodies angainst the antibiotics: an overview. Ann. Ist. Super. Sanita. 1991, vol. 27, No. 1, pp. 149-154.*

(Continued)

*Primary Examiner* — Shafiqul Haq
(74) *Attorney, Agent, or Firm* — Pyprus Pte Ltd

(57) ABSTRACT

The present invention provides a hapten derivative and conjugate of a natural high intensity sweetener containing hydroxyl groups. The conjugate can be used to produce antibodies specific against the natural high intensity sweetener. The present invention further provides a kit and method for detecting and quantifying the natural high intensity sweetener in a sample.

6 Claims, 6 Drawing Sheets (1)

(2)

(56) References Cited

OTHER PUBLICATIONS

Westermann et al. Simple, rapid and sensitive determination of epinephrine and norepinephrine in urine and plasma by non-competitive enzyme immunoassay, compared with HPLC method. Clin. Lab. 2002, vol. 48, pp. 61-71.*

Woelwer-Riech et al. Improved HPLC method for the evaluation of the major steviol glycosides in leaves of Stevia rebaudiana. Eur Food Res Technol 2010, vol. 231, pp. 581-588.*

Kawai et al., "Immunochemical detection of flavonoid glycosides: Development, specificity, and application of novel monoclonal antibodies", Archives of Biochemistry and Biophysics, 476 (2008), pp. 124-132.

Tothiam, C. et al., "An Enzyme-Linked Immunosorbant Assay Using Monoclonal Antibody Against Bacoside A3 for Determination of Jujubogenin Glycosides in Bacopa monnieri (L.) Wettst." Phytochemical Analysis, 2011, vol. 22, pp. 385-391, First published online Mar. 17, 2011.

Sreenath, K. et al., "Quantification of Xylitol in Foods by an Indirect Competitive Immunoassay." Journal of Agricultural and Food Chemistry, 2010, vol. 58, pp. 1240-1246.

Hegde, V. L. et al., "Generation of antibodies specific to D-mannitol, a unique haptenic allergen using reductively aminated D-mannose-bovine serum albumin conjugate as the immunogen." Immunobiology, 2007, vol. 212, pp. 119-128.

Sreenath, K. et al., "Analysis of erythritol in foods by polyclonal antibody-based indirect competitive ELISA." Analytical Bioanalytical Chemistry, 2008, vol. 391, pp. 609-615.

Linthicum, D. S. et al., "Antibody-based Fluoresence Polarization Assay to Screen Combinatorial Libraries for Sweet Taste Compounds." Combinatorial Chemistry and High Throughput Screening, 2001, vol. 4, pp. 431-438.

Phrompittayarat, W. et al., "Determination of Pseudojujubogenin Glycosides from Brahmi Based on Immunoassay Using a Monoclonal Antibody Against Bacopaside I." Phytochemical Analysis, 2007, vol. 18, pp. 411-418.

International Search Report of international patent application No. PCT/MY2011/000209 completed on Feb. 16, 2012 and mailed on the same day ( 5 pages ).

Written Opinion of international patent application No. PCT/MY2011/000209 completed on Feb. 16, 2012 ( 6 pages ).

International Search Report of international patent application No. PCT/MY2012/000138 completed on Oct. 22, 2012 and mailed on the same day ( 4 pages ).

Written Opinion of international patent application No. PCT/MY2012/000138 completed on Oct. 22, 2012 ( 5 pages ).

* cited by examiner

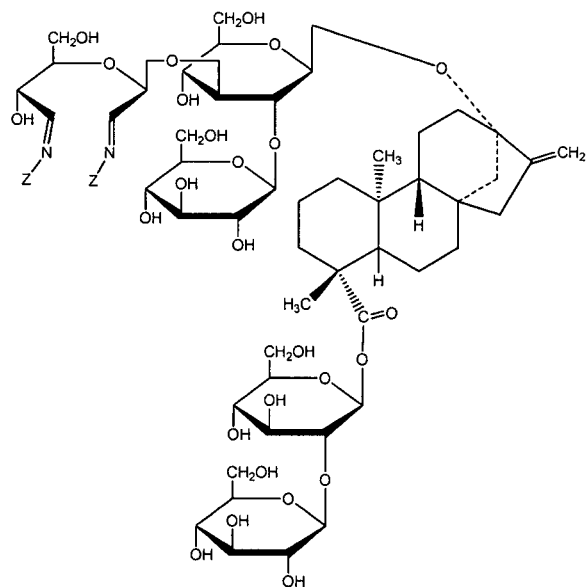
(1)
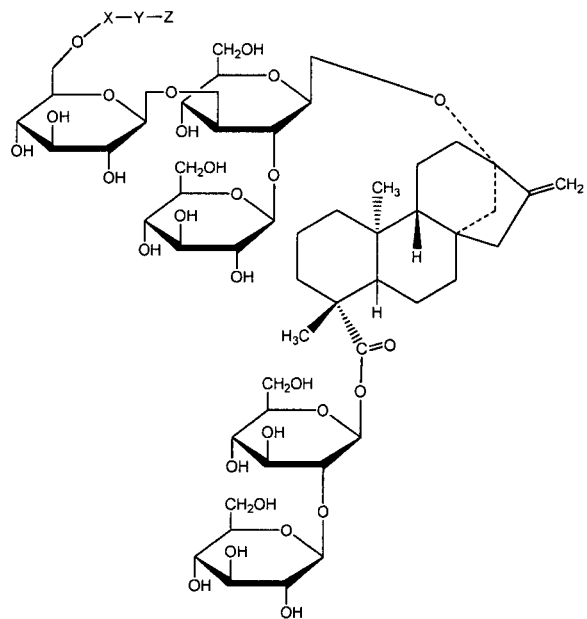
(2)
FIG 2

*a)* Immobilized Antibody Format

1. Competitive reaction

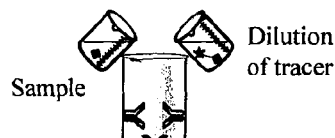

Concentration of Reb D

Low    High

2. Reveal reaction

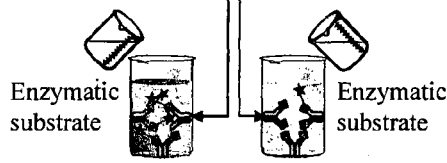

3. Results

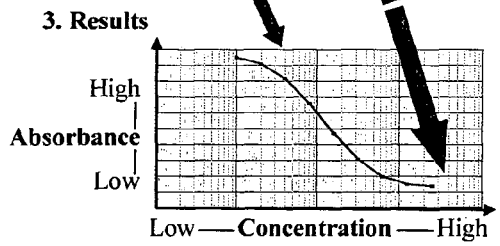

- Y Antibody against Reb D
- • Reb D
- •— Conjugate protein-hapten
- •— Tracer conjugate hapten-HRP enzyme
- 🟊 Tracer secondary antibody linked to HRP enzyme (GAR-HRP)

*b)* Immobilized Coating Conjugate Format

1. Competitive reaction

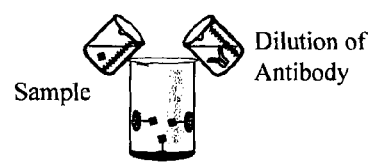

Concentration of Reb D

Low    High

2. Addition of GAR-HRP

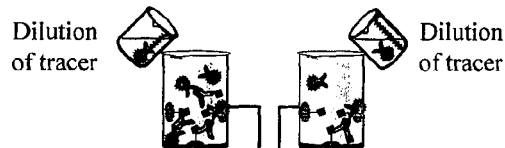

3. Reveal reaction

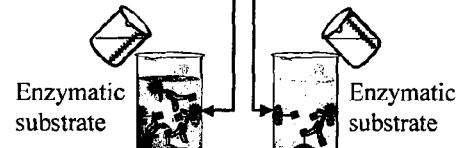

4. Results

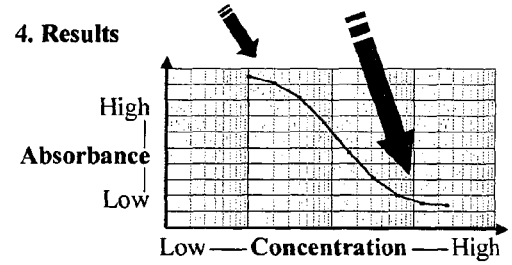

FIG 7

METHOD AND SYSTEM FOR DETECTION OF NATURAL HIGH INTENSITY SWEETENERS THAT CONTAIN HYDROXYL GROUPS

FIELD OF INVENTION

The present invention relates to method and system for the detection of steviol glycosides.

BACKGROUND OF THE INVENTION

High intensity sweeteners possess a sweetness level many times exceeding that of sucrose. They are widely used in diet and calorie-reduced food as being essentially non-caloric, not affecting blood glucose level, and provide little or no nutritive value. In contrast, natural caloric sweeteners such as sucrose, fructose, and glucose are not suitable for diet and calorie-reduced food for being highly caloric, even though they provide the most desirable taste to consumers.

*Stevia rebaudiana* Bertoni is a perennial shrub of the Asteraceae (Compositae) family native to certain regions of South America. The leaves of the plant contain from 10 to 20% of diterpene glycosides, which are around 150 to 450 times sweeter than sugar. The leaves have been traditionally used for hundreds of years in Paraguay and Brazil to sweeten local teas and medicines.

At present there are more than 230 *Stevia* species with significant sweetening properties. The plant has been successfully grown under a wide range of conditions from its native subtropics to the cold northern latitudes.

The extract of *Stevia rebaudiana* plant contains a mixture of different sweet diterpene glycosides, which have a single base—steviol and differ by the presence of carbohydrate residues at positions $C_{13}$ and $C_{19}$. These glycosides accumulate in *Stevia* leaves and compose approximately 10%-20% of the total dry weight. The steviol glycosides include Dulcoside A, Rebaudiosides A, B, C, D, E, and F, steviolbioside, and Rubusoside. Typically, on a dry weight basis, the four major glycosides found in the leaves of *Stevia* are Dulcoside A (0.3%), Rebaudioside C (0.6-1.0%), Rebaudioside A (3.8%) and Stevioside (9.1%). Among steviol glycosides only Stevioside and Rebaudioside A are available in commercial scale.

Steviol glycosides have zero calories and can be used wherever sugar is used. They are ideal for diabetic and low calorie diets. In addition, the sweet steviol glycosides possess functional and sensory properties superior to those of many high potency sweeteners.

Rebaudioside D (CAS No: 63279-13-0) is one of the sweet glycosides found in *Stevia rebaudiana*.

Studies show that highly purified forms of Rebaudioside D possess very desirable taste profile, almost lacking bitterness, lingering licorice aftertaste typical for other Steviol glycosides. These properties multiply the significance of Rebaudioside D and attract great interest for methods of preparation of highly purified forms of Rebaudioside D.

It has to be noted that in commercially available *Stevia rebaudiana* varieties rebaudisoide D content is very low. Generally on a dry weight basis the leaves of *Stevia rebaudiana* contain 0-0.1% rebaudioside D. Therefore there's a need of developing new varieties of *Stevia rebaudiana* with higher content of rebaudioside D. One of the key conditions for such development work is the availability of simple and high throughput testing methodologies, which can be applied on a large number of samples.

On the other hand, the testing methodologies which exist today for steviol glycosides' analysis employ very sophisticated and expensive HPLC techniques with very low throughput. These methods, although robust and well established, are time consuming, expensive, require specialised technicians and instrumentation, and the number of samples that can be processed daily is small. In addition, the amounts of chemicals and toxic solvents that are used often have a high environmental risk.

These disadvantages clearly show the need for developing fast, easy-to-use, robust, sensitive and cost-effective techniques for high throughput analysis of steviol glycosides, particularly rebaudioside D in various matrices, including plant biomass.

SUMMARY OF THE INVENTION

One aspect of the present invention provides a hapten derivative of a natural high intensity sweetener containing hydroxyl groups. In one embodiment, the hapten derivative has the structure selected from the group consisting of:

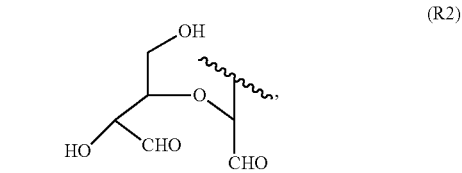

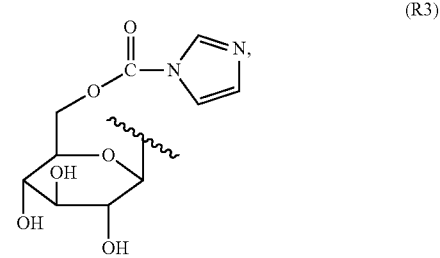

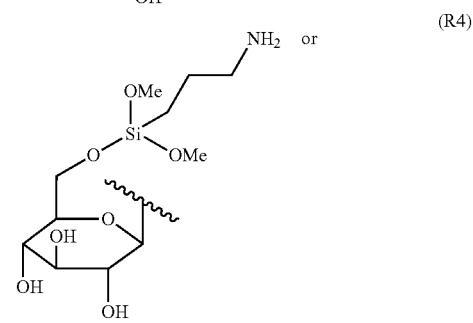

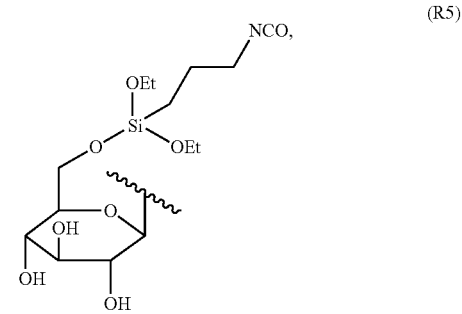

wherein the hapten derivative is used for further making conjugates for being used as an immunogen for generating antibodies specific for the natural high intensity sweetener or a reagent for detecting the natural high intensity sweetener.

In another embodiment of the hapten derivative, the natural high intensity sweetener is selected from the group consisting of Dulcoside A, Rebaudiosides A, B, C, D, E, and F, Steviolbioside and Rubusoside.

In another embodiment of the hapten derivative, the R2 is formed by reacting the natural high intensity sweetener with sodium periodate.

In another embodiment of the hapten derivative, the R3 is formed by reacting the natural high intensity sweetener with N,N'-carbonyldiimidazole.

In another embodiment of the hapten derivative, the R4 is formed by reacting the natural high intensity sweetener with 3-aminopropyltrimethoxysilane.

In another embodiment of the hapten derivative, the R5 is formed by reacting the natural high intensity sweetener with (3-propilisocianate)triethoxysilane.

Another aspect of the present invention provides a conjugate of a natural high intensity sweetener containing hydroxyl groups. In one embodiment, the conjugate has the structure of formula (1) and (2). Both structures are a simplified representation of the possible conjugates, as all the sugar rings are susceptible of suffering that chemical modification, wherein X is a linker chain comprising 1-8 carbon or hetero atoms; Y is selected from the group consisting of —CO, —NH$_2$ and —NCO; and Z is an antigenic carrier or a label; and wherein the conjugate is used as an immunogen for generating antibodies specific for the natural high intensity sweetener or a reagent for detecting the natural high intensity sweetener.

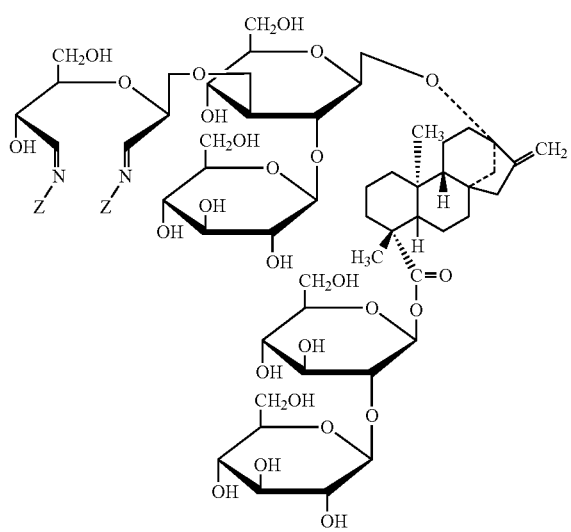

(1)

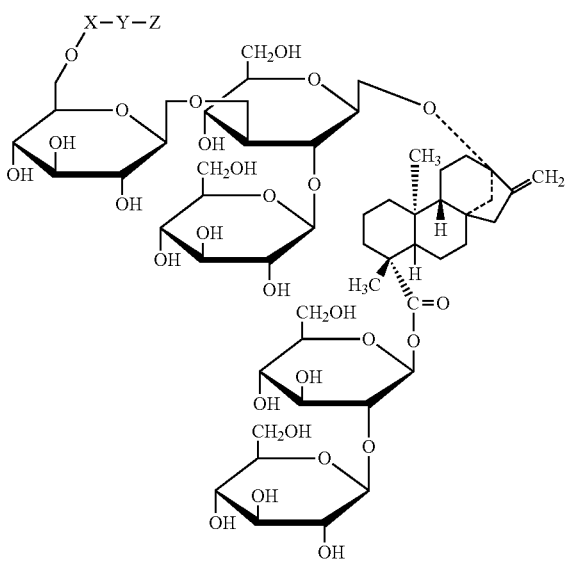

(2)

In another embodiment of the conjugate, the linker chain is substituted or unsubstituted.

In another embodiment of the conjugate, the linker is straight or branched.

In another embodiment of the conjugate, X is —Si(OMe)$_2$—CH$_2$—CH$_2$—CH$_2$.

In another embodiment of the conjugate, Y is —NH$_2$.

In another embodiment of the conjugate, the label is selected from the group consisting of radioactive isotopes, enzymes, enzyme fragments, enzyme substrates, enzyme inhibitors, coenzymes, catalysts, fluorophores, dyes, chemiluminescers, luminescers, sensitizers, non-magnetic or magnetic particles, solid supports, liposomes, ligands, receptors and hapten radioactive isotopes.

In another embodiment of the conjugate, the natural high intensity sweetener is selected from the group consisting of Dulcoside A, Rebaudiosides A, B, C, D, E, and F, steviolbioside, and Rubusoside.

Another aspect of the present invention provides a kit for detecting a natural high intensity sweetener containing hydroxyl groups. In one embodiment, the kit comprises a conjugate of the natural high intensity sweetener with a detectable label as a tracer; an antibody specific against the natural high intensity sweetener; and optionally a detectable enzymatic substrate if the detectable label is an enzyme; wherein the antibody is coated onto a support; and wherein when the sample containing the natural high intensity sweetener is contacted with the tracer first to form a mixture and the mixture is then contacted with the coated antibody, the quantity of the tracer bound to the coated antibody is inversely correlating with the concentration of the natural high intensity sweetener in the sample.

In another embodiment of the kit, the detectable label is selected from the group consisting of radioactive isotopes, enzymes, enzyme fragments, enzyme substrates, enzyme inhibitors, coenzymes, catalysts, fluorophores, dyes, chemiluminescers, luminescers, sensitizers, non-magnetic or magnetic particles, solid supports, liposomes, ligands, receptors and hapten radioactive isotopes.

In another embodiment of the kit, the natural high intensity sweetener is selected from the group consisting of Dulcoside A, Rebaudiosides A, B, C, D, E, and F, steviolbioside, and Rubusoside.

Another aspect of the present invention provides a method for detecting a natural high intensity sweetener containing hydroxyl groups in a sample. In one embodiment, the method comprises providing a conjugate of the natural high intensity sweetener with a detectable label as a tracer; contacting the tracer with the sample to form a mixture; providing an antibody specific against the natural high intensity sweetener, wherein the antibody is coated onto a solid support; contacting the mixture with the coated antibody; and optionally providing a detectable enzymatic substrate if the detectable label is an enzyme; wherein the quantity of the tracer bound to the coated antibody is inversely correlating with the concentration of the natural high intensity sweetener in the sample.

Another aspect of the present invention provides a kit for detecting a natural high intensity sweetener containing hydroxyl groups. In one embodiment, the kit comprises a conjugate of the natural high intensity sweetener; an antibody specific against the natural high intensity sweetener, wherein the antibody is conjugated with a detectable label; and optionally a detectable enzymatic substrate if the detectable label is an enzyme; wherein the conjugate is coated onto a support; and wherein when the sample containing the natural high intensity sweetener is contacted with the antibody first to form a mixture and the mixture is then contacted with the coated conjugate, the quantity of the antibody bound to the coated conjugate is inversely correlating with the concentration of the natural high intensity sweetener in the sample.

Another aspect of the present invention provides a method for detecting a natural high intensity sweetener containing hydroxyl groups. In one embodiment, the method comprises providing a conjugate of the natural high intensity sweetener that is coated onto a solid support; providing an antibody specific against the natural high intensity sweetener, wherein the antibody is conjugated with a detectable label; contacting the antibody with a detectable label with the sample to form a mixture allowing the natural high intensity sweetener in the sample to react with the antibody first; contacting the mixture with the coated conjugate; and optionally providing a detectable enzymatic substrate if the detectable label is an enzyme; wherein the quantity of the antibody bound to the coated conjugate is inversely correlating with the concentration of the natural high intensity sweetener in the sample.

Additional features of the present invention will become apparent to those skilled in the art, upon consideration of the following detailed description of preferred embodiments exemplifying the best mode of carrying out the invention as presently perceived.

BRIEF DESCRIPTION OF THE FIGURES

The accompanying drawings are included to provide a further understanding of the invention. The drawings illustrate embodiments of the invention and together with the description serve to explain the principles of the embodiments of the invention. Preferred embodiments according to the present invention will now be described with reference to the Figures, in which like reference numerals denote like elements.

FIG. 2 shows the structures (Formula 1 and 2) of an illustrative Rebaudioside D derivative of the present invention.

FIG. 7 shows immunoassay formats.

DETAILED DESCRIPTION OF THE INVENTION

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

Immunoassays (IAs) can analyze and monitor many targets at desirable or regulatory levels without any or minimal sample preparation. The strength of IAs lies in their capability of screening of a large number of samples within a short time, being a valuable supplement to other analytical methods.

Immunoassays have been widely and successfully used in clinical chemistry and veterinary drug registration for many years. Extensive literature is available which indicates the potential of immunoassays as fast, reliable and cost efficient methods in residue analysis of different analytes. In contrast, the development of immunoassays by industries and their acceptance by registration agencies as analytical methods for the monitoring of agrochemical residues is scarce.

All immunoassays rely on the interaction between an antibody and a target analyte. Antibodies are produced in response to an immunogen by a complex mechanism. Approximately 90% of the developed immunoassays for residue analyses use the Enzyme-Linked Immunosorbent Assay (ELISA). In this technique the analyte from the sample and a known amount of enzyme-tagged analyte compete for a limited number of antibody binding sites. Quantification is achieved by comparing the signal generated by an unknown sample with a standard curve.

In water, ELISA assays are generally used as fast stand-alone methods. In solid matrices they usually serve as detectors in sample extracts with or without clean-up step. In this matter, immunoassays are able to detect low concentrations in many samples in a short time, and often do not require laborious extraction or cleanup steps, making its particularly suitable for screening purposes.

The present invention attempted to develop a method and system for detection and quantification of natural high intensity sweeteners that contain hydroxyl groups. For example, the natural high intensity sweeteners from *Stevia* includes Dulcoside A, Rebaudiosides A, B, C, D, E, and F, steviolbioside, and Rubusoside. The exemplary natural high intensity sweetener is Rebaudioside D (RebD). It is to be noted that RebD is used for the sole purpose to illustrate the principles of the present invention; by no means, the present invention is limited to RebD.

Figure 1:
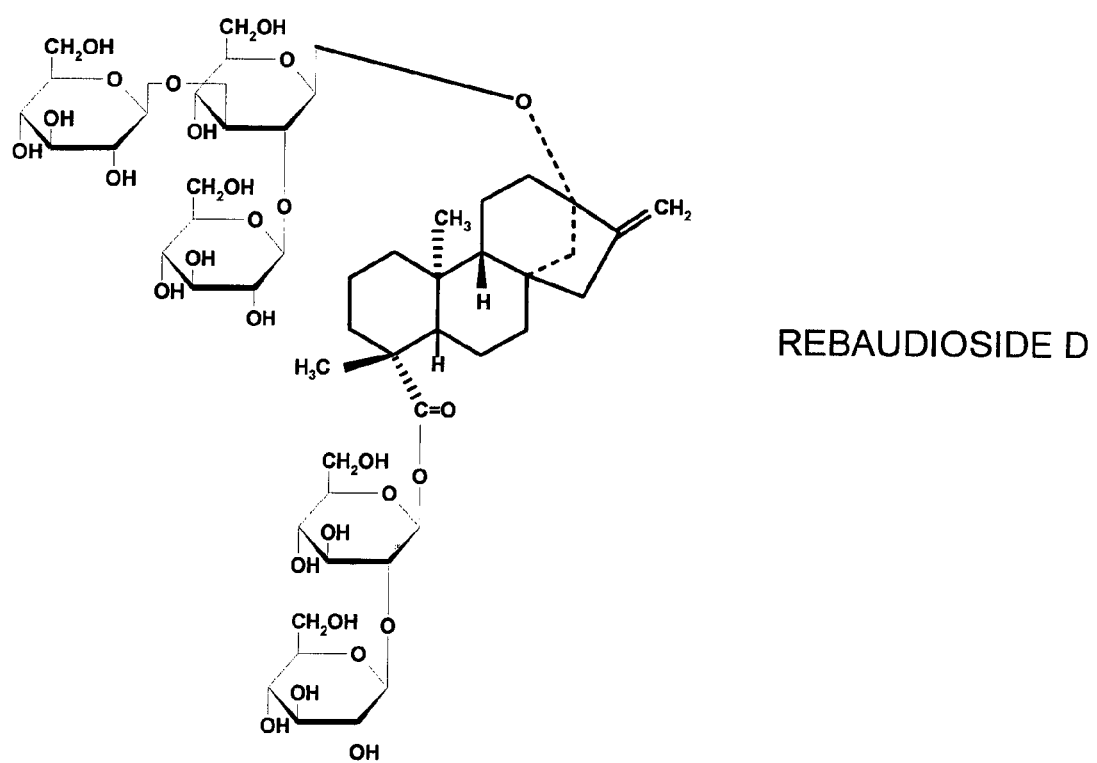
FIG. 1 shows the structure of Rebaudioside D (CAS No: 63279-13-0), designated as $R_1$ hapten.

RebD (CAS No: 63279-13-0) is one of the sweet glycosides found in *Stevia rebaudiana*, and has the structure as shown in FIG. 1.

RebD itself is not immunogenic (hapten). As is a hapten, RebD needs to be conjugated to a protein carrier so that RebD-specific antibodies can be produced. The inventors of the present invention found that RebD could not be conjugated readily to a protein carrier. After extensive exploration, the inventors of the present invention discovered that RebD could be first activated through its hydroxyl group (RebD derivative haptens) and then the activated RebD derivatives could be readily conjugated with a protein carrier. The RebD derivative-protein conjugates are able to produce RebD-specific antibodies. Then, the RebD-specific antibodies can be used to develop methods and systems for RebD detection and quantification.

"Haptens" are partial or incompletes antigens. They are usually protein-free substances, mostly of low molecular weight, which alone are not capable of stimulating antibody formation, but which do react with antibodies. Hapten-specific antibodies may be formed by coupling a hapten to a high molecular weight antigenic carrier (macromolecule) and then injecting this coupled product, i.e., immunogen, into a human or animal subject. In the present invention, RebD is designated as $R_1$ hapten, and RebD derivative haptents are designated as haptens $R_2$-$R_5$ that were synthesized by chemical derivatisation of RebD (detailed discussion of haptens $R_2$-$R_5$ is provided hereinafter).

In one embodiment, the present invention provides a hapten-carrier conjugate having the following structure (Formula 2) (FIG. 2):

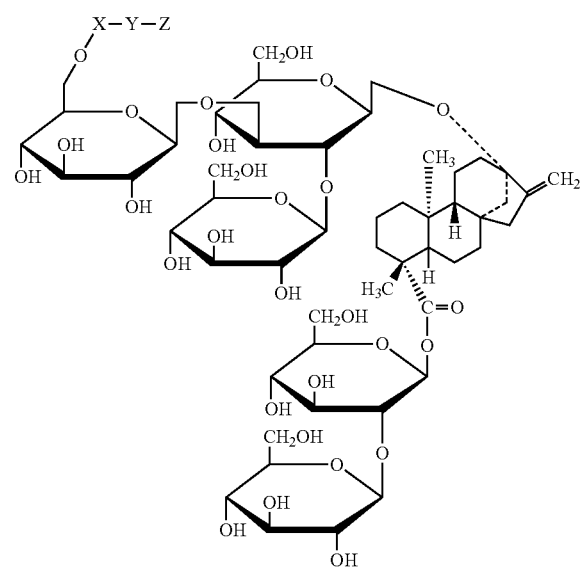

(2)

X is a linker chain comprising 1-8 carbon or hetero atoms, wherein the linker chain may be substituted or unsubstituted and may be straight or branched. Y is selected from the group consisting of —CO, —NH$_2$, and NCO—; and Z is an antigenic carrier or a label.

In one particular illustrative embodiment, X is —Si(OMe)$_2$—CH$_2$—CH$_2$—CH$_2$, Y is —NH$_2$, and Z is the antigenic carrier. Antibodies produced using such compounds and immunoassay kits using the antibodies are also provided.

The phrase "antibody capable of specifically binding Rebaudioside D" as used herein refers to an antibody that is of capacity to react with at least one epitope within RebD in a true antibody-antigen reaction forming an antibody-antigen complex, as opposed to non-specific interaction.

The term "analog" or "derivative" refers to a chemical compound or molecule made from a Rebaudioside D parent compound or molecule by one or more chemical reactions.

An "activated hapten" refers to a hapten derivative that has been provided with an available site for reaction, such as by the attachment of a linking group, for synthesizing a hapten derivative conjugate.

As used herein, a "linking group" or "linker" refers to a portion of a chemical structure that connects two or more substructures such as haptens, carriers, immunogens, labels, tracers, or other linkers. A linking group has at least one uninterrupted chain of atoms other than hydrogen (or other monovalent atoms), extending between the substructures. The atoms of a linking group and the atoms of a chain within a linking group are themselves connected by chemical bonds. Linkers may be straight or branched, saturated or unsaturated carbon chains. They may also include one or more heteroatoms within the chain or at termini of the chains. By "heteroatoms" it is meant atoms other than carbon atoms, illustratively oxygen, nitrogen and silicon, not limited to others as sulfur or phosphorus. The linking group may also include cyclic or aromatic groups as part of the chain or as a substitution on one of the atoms in the chain. The number of atoms in a linking group or linker is determined by counting the atoms other than hydrogen. The number of atoms in a chain within a linking group is determined by counting the number of atoms other than hydrogen along the shortest route between the substructures being connected. Linking groups may be used to activate a hapten, e.g. provide an available site on a hapten for synthesizing a conjugate of a hapten with a label or carrier.

The terms "immunogen" and "immunogenic" as used herein refer to substances capable of producing or generating a strong immune response in a mammalian organism. Sometimes used synonymously with antigen.

A "carrier" or "immunogenic carrier," as the terms are used herein, is an immunogenic substance, commonly a protein, that can join with a hapten, thereby enabling the hapten to induce an immune response and elicit the production of antibodies that can bind specifically with the antigen (hapten). Carrier substances include proteins, glycoproteins, complex polysaccharides, particles and nucleic acids that are recognized as foreign and thereby elicit an immunologic response from the host. Various proteins may be employed as a poly (amino acid) immunogenic carrier. These proteins include albumins and serum proteins, e.g., globulins, ocular lens proteins, lipoproteins, etc. Illustrative proteins include bovine serum albumin (BSA), keyhole limpet hemocyanin (KLH), egg ovalbumin (OVA), bovine gamma-globulin (BGG), etc.

A "label", "detector molecule", or "tracer" is any molecule that produces, or can be induced to produce, a detectable signal. The label can be conjugated to an analyte, an immunogen, an antibody; illustratively the antibody produced in response to the antigenic compound or a secondary antibody having specificity against first one antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, sensitizers, non-magnetic or magnetic particles, solid supports, liposomes, ligands, receptors and hapten radioactive isotopes.

The term "antigenic compound" as used herein is a compound used to produce an immune response. Illustratively, the antigenic compound is a hapten, for example Rebaudioside D, linked to an immunogenic carrier. The antigenic compound is used to generate the desired antibodies.

The term "labeled competitor" or "conjugate" as used herein is forming by covalently coupling two molecules together such as a hapten with a protein or a detectable label or tracer capable of specific binding to antibodies having specificity for Rebaudioside D. Illustratively, the molecule is Rebaudioside D or a derivative or analyte thereof.

A "substrate" is a chemical that specifically reacts with an enzyme.

The term "sample" includes, but not limited to, any quantity of a substance from plant biomass or foods.

Accordingly, developed assays may provide sensitivity across a broader range of Rebaudioside D concentrations.

Numerous quantitative immunoassay formats for detecting a hapten or other small molecule in a sample are known. An assay method for Rebaudioside D illustratively includes combining the sample with an anti-rebaudioside D antibody and detecting the amount of the anti-rebaudioside D antibody-rebaudioside D complex, as indicative of the amount of Rebaudioside D in the sample.

Illustrative immunoassays employ polyclonal antibodies, non-limiting for monoclonal antibodies, with appropriate sensitivity and specificity to Rebaudioside D to provide information about Rebaudioside D concentrations, statistically comparable to that obtained through analytical methods such as HPLC. Such immunoassays illustratively are useful in monitoring levels of the sweet glycosides in plant biomass.

Designing an immunoassay for the detection of a small molecule such as Rebaudioside D can be a challenge. Such small molecules often lack antigenicity, making it difficult to generate antibodies. To increase the immunogenicity, larger antigenic compounds, illustratively proteins or polypeptides, including but not limited to bovine serum albumin, ovalbumin, keyhole limpet hemocyanin, and the like, are conjugated to the analyte of interest. Further, detection of the target analyte in an immunoassay generally requires the use of a detectable label conjugated to an antibody, an analyte, or analyte analog.

Immunogens may be made by coupling Rebaudioside D to an antigenic carrier protein through a spacer arm. However, it has been found that an extended linker between the antigenic carrier leads to the production of more sensitive antibodies. Without being bound to any particular theory, presumably, the longer linker provides for a more accessible epitope, resulting in increased specificity of the antibody for Rebaudioside D.

BSA-hapten and KLH-hapten, were used as immunogens, HRP-hapten, goat anti-rabbit immunoglobulins-HRP (GAR-HRP) as enzymatic tracer and Hb-hapten, OVA-hapten and BSA-hapten as coating conjugates.

It is understood that any combination of antibodies produced using the above-described antigenic compounds and the above-described labeled competitors may be used in competitive assays, the choice of which depends on the specific assay and desired sensitivity.

Traditionally, detection of low-molecular-mass analytes (haptens) such as Rebaudioside D in solution must employ competitive immunoassay formats. There are two different competitive formats available, (1) with immobilized antibody (FIG. 7a) and (2) with immobilized coating conjugate (FIG. 7b) onto the surface of each micro-well in a 96-well micro plate and held in place via non-covalent bonds between the hydrophobic regions of the protein and the non-polar plastic surface. In format (1), analyte and labeled analyte (tracer) compete for the free antibody binding sites. After removal of unbound reactants the bound tracer yields a signal. The format (2) employs an immobilized hapten-carrier conjugate on the solid phase to which analyte and antibody are added. Antibody binds to the free analyte or to the immobilized hapten in certain ration of the reactants concentration. If a labeled antibody is used, the amount of antibody bound to the solid phase can be directly determined after a washing step. Alternatively, a secondary labeled antibody (such as GAR-HRP) may be used to detect the bound antibody. In these competitive immunoassay formats, the signal is inversely proportional to the amount of free analyte in the sample. In enzyme labeled competitive immunoassay, separation of unbound reagent from bound reagent is needed, i.e. heterogeneous assay is performed.

The derivatives, antibodies, immunogens, and/or other conjugates described herein are also suitable for use with any of a number of other homogeneous and heterogeneous immunoassays with a range of detection systems. The examples presented herein are not intended to be limiting.

Thus, the present invention provides Rebaudioside D derivatives that are useful for the preparation of immunogens and conjugates for use in immunoassays for the detection of Rebaudioside D. By coupling a Rebaudioside D analog according to the present invention to an immunogenic carrier material, polyclonal or monoclonal antibodies can be produced and isolated, which are useful reagents for immunoassays for the detection of Rebaudioside D.

The term "polyclonal antibodies" as used herein is a population of antibodies with various selectivities and affinities produced by many clones of antibody-producing cells.

The term "monoclonal antibodies" as used herein refer to a homogeneous antibody population, possessing identical selectivity and affinity produced by a single clone of antibody-producing cells.

Illustrative Rebaudioside D immunoassays employ anti-Rebaudioside D antibodies that can be either polyclonal or monoclonal. In illustrative competitive immunoassays, the antibody preparation used is induced by an immunogen described herein is formulated in an aqueous solution such as buffer, and the like or provided in an adjuvant or similar composition. The induced antibodies can be tested to determine specificity for Rebaudioside D.

The following examples are provided for the sole purpose of illustrating the principles of the present invention; it by no means shall be interpreted for limiting the scope of the present invention.

EXAMPLE I

Figure 3:
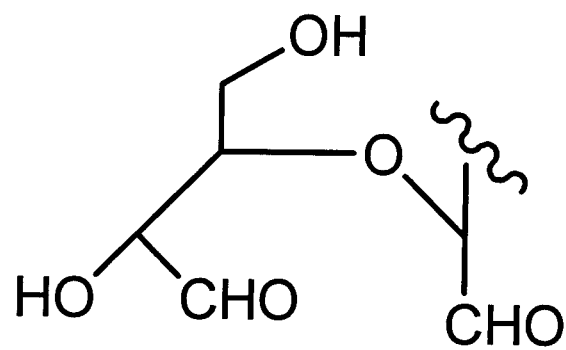
FIG. 3 shows the structure of $R_2$ hapten.

Synthesis of Modified RebDs as RebD Haptens, Labeled RebD haptens as RebD competitors, and RebD hapten-protein conjugates I.1. RebD Hapten $R_2$ and Protein-$R_2$ Conjugate Rebaudioside D (5 mg) was dissolved in 1.2 mL of distilled water. Then, 0.1 M sodium periodate in 10 mM PBS (300 mL) was added, and the reaction mixture was incubated for 20 minutes at room temperature, obtaining the RebD hapten $R_2$ (FIG. 3).

For synthesis of protein-$R_2$ conjugates, proteins (10 mg for BSA and KLH or 3 mg in the case of HRP) were dissolved in 1 mL of carbonate buffer and added to the reaction mixture containing the RebD hapten $R_2$, incubating with stirring for 2 h at room temperature. The mixture was cooled at 4° C. and the formed imines were quenched with 100 mL of sodium borhydrure (4 mg/mL in distilled water) for 2 hours at 4° C. The conjugates were purified through a molecular exclusion column (Desalting, Pierce) and protein concentration was determined by Bradford method or by direct measurement of absorbance at 404 nm in the case of the HRP enzyme.

I.2. RebD Hapten $R_3$ and Protein-$R_3$ Conjugate

Figure 4:
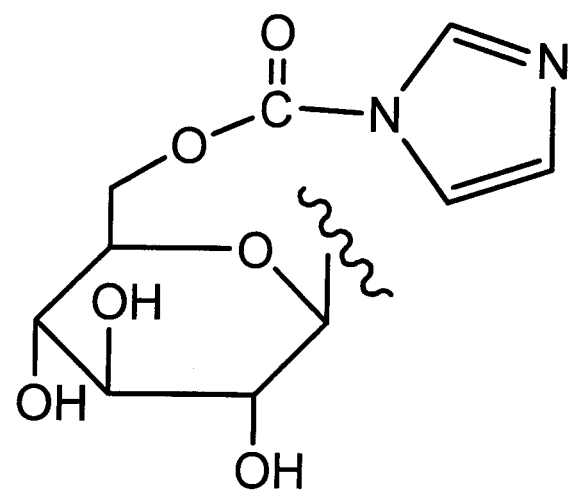
FIG. 4 shows the structure of $R_3$ hapten.

N,N'-carbonyldiimidazole (0.25 mmol, 41 mg) was added into a solution of Rebaudioside D (0.042 mmol, 47 mg) in anhydrous dimethylformamide (0.5 mL) under inert atmosphere at 0° C., incubating for 3.5 hours, obtaining RebD hapten $R_3$ (FIG. 4) After this, 0.25 mL of the reaction mixture was added to a protein solution (15 mg BSA or 10 mg of KLH in 1.8 mL of carbonate buffer) and incubated at 4° C. for 48 hours. The conjugates were purified and the protein concentration was measured as described above.

I.3. RebD Hapten $R_4$ and Protein-$R_4$ Conjugate

Figure 5:
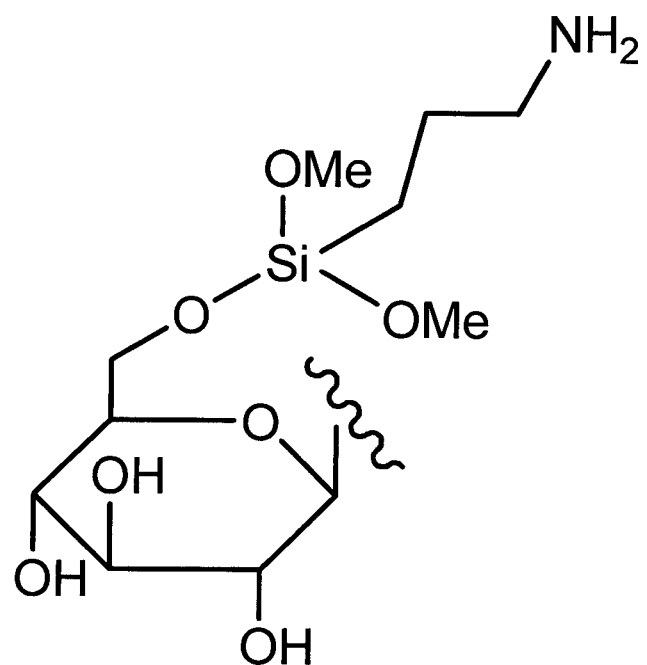
FIG. 5 shows the structure of $R_4$ hapten.

Rebaudioside D (50 mg) was silanised by vapour phase reaction with 3-aminopropyltrimethoxysilane in a chamber, at room temperature for 3 h, obtaining RebD hapten $R_4$ (FIG. 5). The presence of primary amino groups was verified by Sarin method. For the synthesis of protein-$R_4$ conjugates, a solution of protein (10 mg of KLH, BSA, OVA and Hb in 5 mL of 10 mM PBS, or 3 mg of HRP in 1.5 mL of PBS) was provided. Five mg of RebD hapten $R_4$ and glutaraldehyde at 25% (200 mL) were added to the protein solution, leaving the reaction for 4 hours at 4° C. Then, to quench the imines formed, 50 mg of sodium borhydrure was added and left for 1 h at 4° C. These conjugates were used directly without purification.

Figure 6:
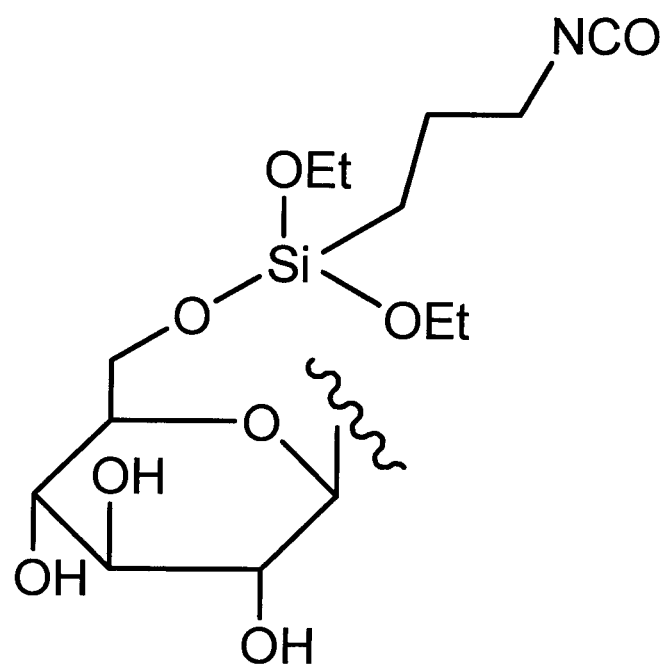
FIG. 6 shows the structure of $R_5$ hapten.

I.4. RebD Hapten $R_5$ and Protein-$R_5$ Conjugate 50 mg of Rebaudioside D was silanised as described for the hapten $R_4$, using as silane (3-propilisocianate)triethoxysilane to obtain RebD hapten $R_5$ (FIG. 6). After 3 hours at room temperature, 5 mg of hapten were added to a protein solution (10 mg of KLH, BSA, OVA and Hb in 5 mL of 10 mM PBS or 3 mg of HRP in 1.5 mL of PBS), leaving the reaction 2 hours at room temperature. In this case the conjugates were also used without purification.

EXAMPLE II

Immunization Schedule and Antiserum Preparation

The hapten $R_1$ (rebaudioside D) (5 mg suspended in 0.5 mL of 10 mM PBS) and KLH-conjugates or BSA-R (n=2-5), (0.5 mL of conjugate at a concentration of 200 mg/mL, 10 mM PBS) were injected intramuscularly into two New Zealand California white rabbits, with 0.5 mL of complete Freund's adjuvant in the first immunization, and 0.5 mL of incomplete Freund's adjuvant in the following. Immunizations were performed every 21 days, and 10 days after each immunization bleedings were carried out to know the title and properties of serum from each animal. After five cycles of immunization, blood was obtained by bleeding, leaving it to coagulate overnight at 4° C. Subsequently, after adding sodium azide (0.02%) serum was separated by centrifugation and stored at −80° C.

Sera obtained were $R_1$ (I and II), BSA-$R_2$ (I and II), KLH-$R_2$ (I and II), BSA-$R_3$ (I and II), KLH-$R_3$ (I and II), BSA-$R_4$ (I and II), KLH-$R_4$ (I and II), BSA-$R_5$ (I and II) and KLH-$R_5$ (I and II). Symbols I and II, denote two white rabbits immunised for each immunogen.

When the schedule was completed, whole blood was collected and allowed to coagulate overnight at 4° C. Then serum was separated by centrifugation and aliquots of sera were stored at 4° C. in 50% ammonium sulphate.

EXAMPLE III

Screening of Sera and Coating Conjugate

The titre of the antisera was determined by checkerboard titration assay, using a non-competitive indirect ELISA.

First, the avidity of the sera obtained against different coating conjugates was determined by non-competitive indirect ELISA using different antisera (serial dilutions from 1/1000 to 1/64000) and concentrations of the coating conjugates (0.001 to 1.0 mg/L). Similarly, the avidity to the enzyme-tracer was determined by a direct non-competitive ELISA using several dilutions of the tracer (serial dilutions from 0.001 to 1.0 mg/L) and serum (from 1/500 to 1/512000).

The titres obtained from conjugate-coated format indirect format (ELISA plates coated with protein-hapten) were higher than those obtained for direct format (ELISA plates coated with serum), choosing as optimal concentrations of coating conjugates and dilution of serum, those that produced absorbance values around 0.8-1.2 units in absence of analyte (Rebaudioside D), to carry out competitive tests.

Serum KLH-$R_3$ (I) showed competition with several coating conjugates. So, the combination KLH-$R_3$ (I)/BSA-$R_3$ (1:2000/0.03 mg/L) was selected, since presented the lowest $IC_{50}$ value (1.30 µg/L) to establish an ELISA for Rebaudioside D.

EXAMPLE IV

Optimization and Performance of ELISA Assay for Rebaudioside D

IV.1. Conjugate-Coated Format

Flat-bottomed polystyrene ELISA plates were coated overnight at 4° C. with 100 µL/well of the appropriate coating conjugate solution in CB. The following day, plates were washed six times with 15 mmol/L PBS-T pH 8.5, and then 50 µL of the serum dilution and 50 µL of Reb D in PBS-T were added and incubated at room temperature during 1 h. After washing, an incubation step (1 h) with 100 µL/well GAR-HRP (diluted 1/2000 in PBS-T) was accomplished, and plates washed again. Finally, 100 µL/well of substrate solution (2 mg/mL OPD and 0.012% $H_2O_2$ in 25 mmol/L sodium citrate and 62 mmol/L sodium phosphate, pH 5.5) was added. The enzymatic reaction was stopped after 10 min by addition of 2.5 mol/L $H_2SO_4$ (50 µL/well), and the absorbance was read in a dual-wavelength mode (490, 650 nm).

IV.2. ELISA Optimization

The optimization was performed for the most sensitive assay (antiserum KLH-$R_3$/BSA-$R_3$ coating conjugate) using Reb D as competitor analyte.

The influence of several experimental parameters such as ionic strength, pH, surfactant concentration and time of competition on assay characteristics was examined in order to improve the immunoassay performance (sensitivity, maximum absorbance, working or dynamic range and detection limit). Criteria used to evaluate the assay performances were sensitivity ($IC_{50}$), maximum absorbance ($A_0$), dynamic range (DR, established between the Reb D concentrations producing 20% and 80% colour inhibition) and limit of detection (LD, estimated at 10% inhibitory concentration).

IV.3. Effect of Ionic Strength

To study the influence of ionic strength, different tests were performed varying the concentration of PBS in the competition buffer, between 5 and 30 mM, 0.05% (v/v) Tween 20, pH 7.5. The maximum signal significantly increased when ionic strength decrease, while the sensitivity ($IC_{50}$) was clearly improved at 15 mM, so this was the selected value of the buffer.

IV.4. Effect of pH

To study the effect of pH on the assay sensitivity and maximum signal, 15 mM, 0.05% (v/v) Tween 20 competition buffer solutions were prepared at different pH (4.5, 5.5, 6.5, 7.5, 8.5 and 9.5). It was observed that the best sensitivity was obtained at pH 8.5.

IV.5. Effect of Surfactant Concentration

The effect of surfactant concentration was studied with different solutions of PBS competition buffer, using the conditions previously optimised (ionic strength and pH), varying the concentration of Tween 20 (0 to 0.25%). The best $IC_{50}$ value was obtained with 0.25% Tween 20. Thus, the optimal parameters for the Reb D immunoassay developed were: 15 mM PBS, pH 8.5, and 0.25% Tween 20 (see Table 1).

TABLE 1

Effect of different parameters on the ELISA performance

| Parameter | $IC_{50}$ (µg/L) | $A_0$ (Absorbance Units) |
|---|---|---|
| PBS (mmol/L) | | |
| 5 | 1.53 ± 0.41 | 2.39 ± 0.22 |
| 10 | 1.30 ± 0.35 | 1.73 ± 0.17 |
| 15 | 0.77 ± 0.24 | 1.49 ± 0.15 |
| 20 | 1.02 ± 0.28 | 1.22 ± 0.13 |
| 30 | 1.70 ± 0.45 | 1.06 ± 0.09 |
| pH | | |
| 4.5 | 0.63 ± 0.21 | 1.19 ± 0.08 |
| 5.5 | 0.86 ± 0.23 | 1.29 ± 0.10 |
| 6.5 | 0.91 ± 0.27 | 1.42 ± 0.14 |
| 7.5 | 0.77 ± 0.24 | 1.49 ± 0.15 |
| 8.5 | 0.49 ± 0.15 | 1.44 ± 0.12 |
| 9.5 | 0.50 ± 0.19 | 1.21 ± 0.09 |
| Tween 20 (%) | | |
| 0.000 | 0.68 ± 0.26 | 1.91 ± 0.21 |
| 0.010 | 0.56 ± 0.23 | 1.59 ± 0.19 |
| 0.025 | 0.58 ± 0.19 | 1.51 ± 0.18 |
| 0.050 | 0.49 ± 0.15 | 1.44 ± 0.12 |
| 0.100 | 0.39 ± 0.08 | 1.20 ± 0.10 |
| 0.250 | 0.36 ± 0.05 | 1.15 ± 0.06 |

Pair KLH-$R_3$ (I)/BSA-$R_3$ (1:2000/0.03 mg/L), PBS-T 15 mmol/L, 0.25% (v/v) Tween 20, pH 8.5, 1 h competition, [GAR-HRP] 1/2000.

IV.6. Performance Under Optimal Conditions

Figure 8:
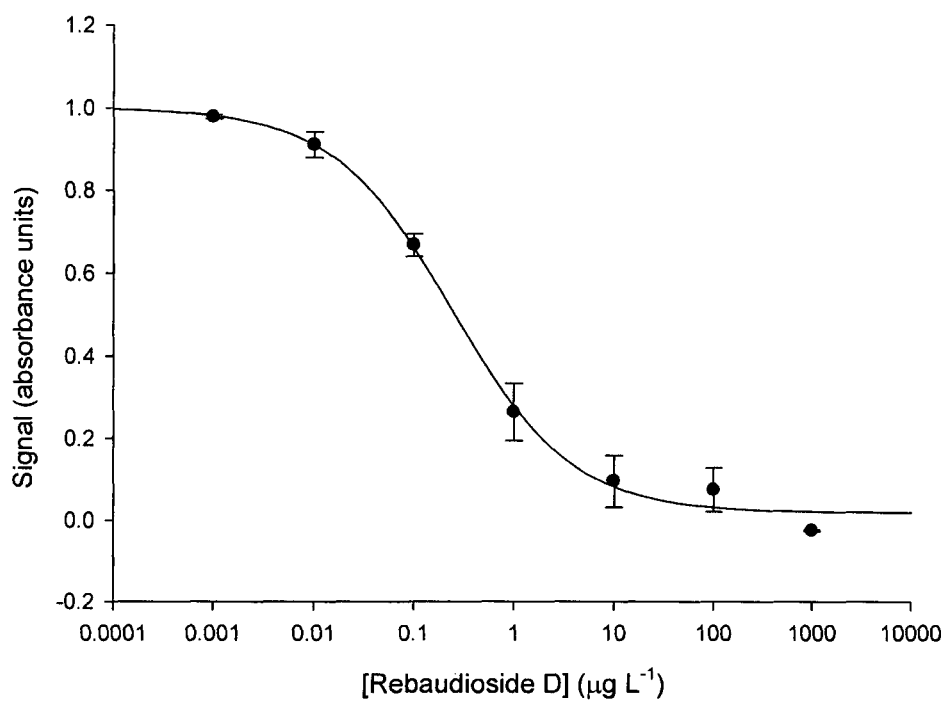
FIG. 8 shows a competitive calibration curve for Rebaudioside D under optimized conditions (n=20).

After the optimization was performed, a set of 20 calibration curves were carried out as shown in FIG. 8, which showed an $IC_{50}$ value of 0.36±0.05 µg/L, a detection limit of 0.01 µg/L, and a dynamic range of 0.04 to 1.91 µg/L for Reb D.

IV.7. Cross-Reactivity Studies

Assay selectivity was evaluated by determining the cross-reactivity with two sugars derived from *Stevia rebaudiana*, such as rebaudioside A and stevioside. The cross reactivity values were calculated according to the following equation: CR=($IC_{50}$ [mg/L] Rebaudioside D/$IC_{50}$ [mg/L] compound)×100.

The interferences observed were negligible for the two compounds tested (CR 0.16% with Rebaudioside A and 8.6×10$^{-5}$% for Stevioside). Thus, the developed immunoassay for Reb D is specific (maximum CR<10%) against different related compounds: Stevioside ($IC_{50}$=418,605 µg/L) and Reb A ($IC_{50}$=225 µg/4 which the highest interference was obtained (0.16%).

EXAMPLE V

Analysis of Real Samples

Three different *Stevia* samples were extracted by two methods and the extracts analysed by HPLC and the developed ELISA.

V.1. Sample Extraction Procedure

For method one, the leaves was dried in a vacuum oven at 40° C. until constant weight (step 1). The dried leaves were grinded to fine powder using laboratory grinder or mill (step 2). Approx. 0.5 g of fine powders were placed in a centrifuge tube, then approx. 10 mL of water were added into the centrifuge tube, and the centrifuge tube was incubated in a shaking water bath at 55° C. for 1 h (step 3). The liquid (supernatant) was separated by centrifugation at 10,000 rpm for 15 min (step 4). The supernatant was filtered through filter paper into 50 mL volumetric flask (step 5). The biomass retained on the filter was returned to the centrifuge tube and subjected to another round of extraction, separation and filtration as described in steps 3-5. In total 5 consecutive extractions were carried out and the filtrates yielded from all extractions were mixed together (step 6). The volume of mixture was adjusted to 50 mL with water. Then the obtained mixture was filtered through 0.2 µm syringe filter into HPLC vial and cap (step 7). Duplicate samples were prepared following steps 3 to 7 (step 8).

For method two, 400 mg of crushed *stevia* leaf samples were placed in an opaque vial, containing 4 mL of acetonitrile:water (50:50). After vigorous agitation, the vial was placed in an ultrasonic bath for 10 min. After that, samples were centrifuged at 15.000 rpm, using the upper phase for analysis.

The extracts obtained from both methods were then properly diluted (1/200, 1/400, 1/600 and 1/1000) (v/v) in PBS 2× and checked for Rebaudioside D with the ELISA described in Example IV. In order to assess assay reproducibility, triplicates of each fortification level were performed. The mean value was compared to HPLC results, and percent recovery calculated. The results are shown in Table 2.

The Rebaudioside D results obtained by HPLC were considered as real values (gold standard) in the leaf samples tested. In this sense, percent recovery (% R) was calculated as (mean ELISA results/HPLC results)×100%.

It is understood that the results of Table 2 are illustrative of one embodiment of ELISA using polyclonal antibody KLH-R3 (I) and BSA-R3 as competitor conjugate. Other competitive assays within the scope of this invention may provide different performance characteristics.

TABLE 2

Results for Reb D obtained for leaf extracts applying two extraction and detection methods

| Sample 1 | | | | Sample 2 | | | | Sample 3 | | | |
|---|---|---|---|---|---|---|---|---|---|---|---|
| Method one | | Method two | | Method one | | Method two | | Method one | | Method two | |
| HPLC | ELISA | HPLC | ELISA | HPLC | ELISA | HPLC | ELISA | HPLC | ELISA | HPLC | ELISA |
| 8.23 | 6.30 | 7.02 | 7.21 | 10.61 | 10.00 | 12:81 | 12.86 | 5 | 6.18 | 3.43 | 3.74 |
| (% R) = 76.5% | | (% R) = 102.7% | | (% R) = 94.2% | | (% R) = 100.4% | | (% R) = 126.6% | | (% R) = 109% | |

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the scope of the present invention. Accordingly, the scope of the present invention is defined by the appended claims and is supported by the foregoing description.

What is claimed is:

1. A conjugate of a natural high intensity sweetener containing hydroxyl groups, said conjugate has the structure of formula (2):

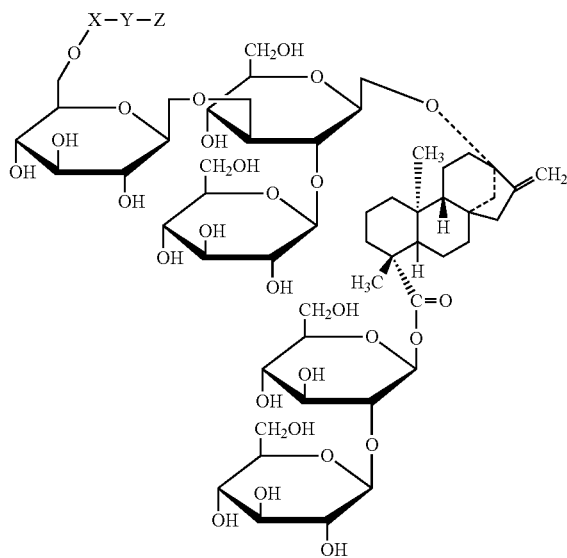

(2)

wherein X is a linker chain comprising 1-8 carbon or hetero atoms; Y is selected from the group consisting of —CO—, —NH—, and —NCO—; and Z is an antigenic carrier or a label; and wherein the conjugate is used as an immunogen for generating antibodies specific for the natural high intensity sweetener or a reagent for detecting the natural high intensity sweetener.

2. The conjugate of claim 1, wherein the linker chain is substituted or unsubstituted.

3. The conjugate of claim 1, wherein the linker chain is straight or branched.

4. The conjugate of claim 1, wherein X is —Si(OMe)$_2$—CH$_2$—CH$_2$—CH$_2$.

5. The conjugate of claim 1, wherein Y is —NH—.

6. The conjugate of claim 1, wherein the label is selected from the group consisting of radioactive isotopes, enzymes, enzyme fragments, enzyme substrates, enzyme inhibitors, coenzymes, catalysts, fluorophores, dyes, chemiluminescers, luminescers, sensitizers, non-magnetic or magnetic particles, solid supports, liposomes, ligands, receptors and hapten radioactive isotopes.

* * * * *